United States Patent [19]

Jablecki

[11] 4,026,275
[45] May 31, 1977

[54] CUTANEOUS SENSITIVITY DIAGNOSTIC DEVICE

[76] Inventor: Charles K. Jablecki, 1422 Damon Court SE., Rochester, Minn. 55901

[22] Filed: Oct. 30, 1975

[21] Appl. No.: 627,072

[52] U.S. Cl. ............................................. 128/2 N
[51] Int. Cl.² ........................................ A61B 5/00
[58] Field of Search ....... 128/2 N, 2 H, 356, 303.1, 128/1.2–1.4, 304

[56] References Cited

UNITED STATES PATENTS

| | | | |
|---|---|---|---|
| 2,095,976 | 10/1937 | Foreman | 128/1.4 |
| 2,517,325 | 8/1950 | Lamb | 128/1.4 |
| 2,546,761 | 3/1951 | Loftus | 128/1.2 |
| 2,706,979 | 4/1955 | Wallace | 128/1.4 |
| 3,185,146 | 5/1965 | Leopoldi | 128/2 N |
| 3,274,995 | 9/1966 | Eidus | 128/303.1 X |

Primary Examiner—Kyle L. Howell
Attorney, Agent, or Firm—Ralph W. Kalish

[57] ABSTRACT

A diagnostic instrument for use in determining the cutaneous sensory capacity of a patient which comprises an elongate body having a bore proceeding from one end and terminating spacedly from the other end. Fitted within said bore is a metallic member having an enlarged head projecting beyond the bore opening for covering the adjacent end of the body. Said body is fabricated of material, such as wood, rubber, plastic or synthetic material having heat transfer properties relatively reduced with respect to the heat conductivity of the metallic member.

11 Claims, 7 Drawing Figures

CUTANEOUS SENSITIVITY DIAGNOSTIC DEVICE

BACKGROUND AND SUMMARY OF THE INVENTION

This invention relates generally to the field of physiological diagnosis and, more particularly, to a diagnostic instrument for determining temperature discrimination.

Heretofore in the field of medical diagnosis, various efforts have been attempted to develop instruments for testing the reaction of a patient to cutaneously received sensations for the purpose of establishing the condition of the peripheral nerves as well as of the central nervous system. One expedient for gaining insight to the condition of the peripheral nerves and the central nervous system is by means of testing cutaneous thermal discrimination. Previously, devices for testing thermal discrimination have required preparation preliminary to usage and in some cases are also cumbersome and must be used at a fixed location, as in a doctor's office. A relatively recent effort for developing testing equipment for this purpose has involved a device incorporating a multiplicity of so-called "thermal discs", but the same are relatively bulky and large, so that patients are usually brought to the device for tests, and also require some preliminary preparation.

Heretofore there has not been available an instrument that requires no preliminary preparation of such limited size as to be amenable to transport, as within a doctor's conventional bag, or even the pocket of a jacket, for testing the temperature responsiveness of the patient's skin.

Therefore, it is an object of the present invention to provide a diagnostic instrument which is of such relatively reduced size that it may be easily carried within the pocket of a physician just as with a pencil, and which instrument is useful in determining the cutaneous thermal discrimination of the patient for providing a key to the state of the patient's peripheral nerves and central nervous system.

It is another object of the present invention to provide an instrument of the character stated which is formed of a marked simplicity of cheaply produced components; which does not involve any moving parts so that the same is durable and resistant to damage through usage.

It is a further object of the present invention to provide an instrument of the character stated which does not necessitate any preliminary conditioning or waiting for usage, being in a constant state of readiness.

It is another object of the present invention to provide an instrument of the character stated which is operated by a physician, physician-in-training, or paramedical personnel, and requiring only the simplest instruction and guidance.

It is another object of the present invention to provide an instrument of the type stated which as indicated above may be most economically manufactured; the use of which obviates costly, elaborate testing equipment as heretofore found in offices and laboratories, and which through its facile portability permits of another area of diagnosis of a patient who may be remote from a hospital or doctor's office.

DESCRIPTION OF THE PREFERRED EMBODIMENT

Figure 2:
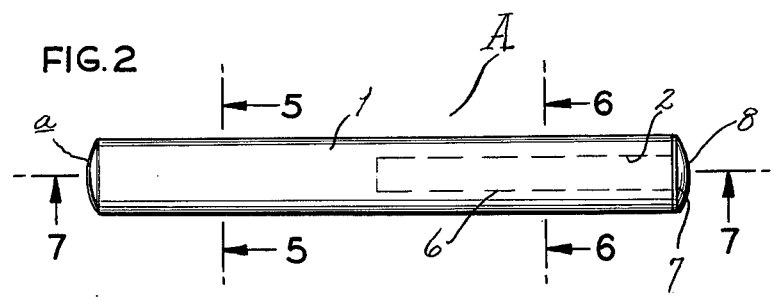
FIG. 2 is a side elevational view.
Figure 7:
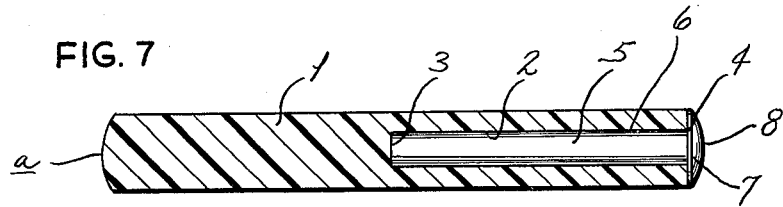
FIG. 7 is a horizontal transverse sectional view taken on the line 7—7 of FIG. 2.

Referring now by reference characters to the drawings which illustrate the preferred embodiment of the present invention, A designates a diagnostic instrument comprising an elongated narrow body fabricated preferably of wood, which may be, desirably, but not necessarily, circular in cross section. Provided within said body 1 is a bore 2, the base of which, as at 3, is located in the intermediate portion of body 1, and which bore opens at its end remote from its base through one end of said body, as at 4. Snugly received, as by a jam fit, within bore 2, is the stem 5 of a metallic component 6, which for purposes of facilitating description will be herein referred to as a "rivet", the inner end of which may abut against bore base 3 and which rivet encompasses a diametrally increased head 7 having a diameter preferably of like extent as the cross section of body 1. As may best be seen in FIGS. 2 and 7, rivet head 7 is endwise rounded, as at 8. The opposite end of body 1 remote from head 7 is also preferably rounded, as at a, with the same curvature as head 7, for purposes presently appearing.

Figure 3:
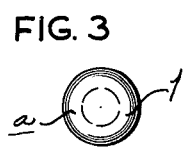
FIG. 3 is an end view of the instrument taken from the left hand side of FIG. 2.
Figure 4:
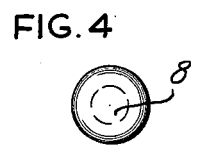
FIG. 4 is an end view taken from the right hand side of FIG. 2.
Figure 5:
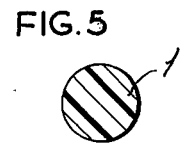
FIG. 5 is a vertical transverse sectional view taken on the line 5—5 of FIG. 2.
Figure 6:
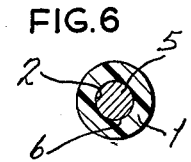
FIG. 6 is a vertical transverse sectional view taken on the line 6—6 of FIG. 2.

As indicated above, body 1 is fabricated desirably of wood but may also be made of plastic, rubber, or other material having recognizedly poor or relatively low heat conductivity properties. Rivet 6 is made of metal having relatively high heat conductivity properties but in any event is of such metal as to effect heat transfer at a rate sufficiently greater than that of the material of construction of body 1 to establish a marked and definitive differential with respect to said body. Accordingly, rivet 6 may be formed of any suitable metal or alloy thereof, such as copper, steel, silver, bronze, etc. It will thus be seen that one end of instrument A is constituted of body 1 (see FIG. 3) while the opposite end is comprised of head 7 of rivet 6; it being observed that said head 7 obscures or prevents exposure of any adjacent portions of body 1.

Figure 1:
FIG. 1 is a perspective view of a diagnostic instrument constructed in accordance with and embodying the present invention, illustrating the same in a condition of use.

As may best be indicated in FIG. 1, instrument A is of such size as to be easily manipulated by the hand of the user, and which may have a length of approximately 4 inches with a cross section of approximately ½ inches. Thus instrument A is relatively small, compact, and of light weight, easily carried in the user's pocket or with an instrument bag. The stem of rivet 6 is, as indicated, substantially ½ the length of body 1 and should, hence, approximate 2 inches for purposes presently appearing. Additionally, with a body of the dimensions above outlined, rivet 6 should desirably have a weight within the range of 14 grams and with the maximum cross section of head 7 being at least ½ inches.

As pointed out hereinabove, the selection of materials of construction for body 1 and rivet 6 is premised upon a differential in the capacity to transfer heat. Therefore, upon contacting a patient's skin with rivet head 7, a distinctly cooler sensation will be experienced than when the opposite end of instrument A is applied to the same location. This differential in sensations results from the fact that body 1, if made of wood, plastic, or rubber, is a poor conductor of heat so that the individual will experience substantially no temperature sensation in view of the fact that heat will not be readily transferred from the skin to such material. On the other hand, when the metallic end of instrument A or rivet head 7 is applied to the patient's skin a relatively cool sensation will be experienced in view of the ready transfer of heat from the contacted body area to the rivet in view of its aforesaid properties.

Therefore, one might term the rivet head 7 of instrument A the "cool" or "cold" end of instrument A and the opposite end consisting of the material body 1 as the "warm" or "hot" end.

In operation, instrument A is to be utilized at room temperature and with the ends being alternatively applied to a selected zone of the patient, such as the face (see FIG. 1) or the dorsum of the hand or the foot. It will be recognized that body temperature is normally above room temperature, there being a difference of between 5° to 10° C. Each end is applied to the select zone for a period of 1 to 2 seconds, and a normal individual will readily indicate to the operator whether one end feels cooler than the other. Clearly the metallic end will be the one indicated as cooler unless the patient is suffering diminution in, or loss of, cutaneous sensory capacity, such as patients with peripheral neuropathy. Thus, the operator will alternatingly apply the different ends to the patient to obtain a percentage of correct answers which percentage quantitates the integrity of a patient's temperature discrimination. It has been found that a range of above 50% and up to 100% is correct so as to eliminate the possibility that a patient might correctly guess ½ of the choices by chance alone.

Because the test depends upon the temperature differential between the patient's body and instrument A, which latter will be at room temperature, it is important that if the patient's hands or feet are cold, the same should be warmed to body temperature before testing.

From the foregoing one may readily appreciate that rivet 6 has certain critical design aspects; one being that the surface area provided by head 7 be of adequate extent so as to make contact with a sufficient area of the patient's skin so that enough nerve endings are engaged to make the test effective since engagement with a relatively small zone could be misleading. A surface area greater than 1 centimeter square gives reproducible results on the dorsum of the patient's foot, which zone is the least sensitive. Areas of less extent, although effective on the face and possibly upon the hand would not have the reliability if applied to the dorsum of the foot.

In addition to the exposed surface area of rivet 6 the same must be of sufficient mass so that the same will not rapidly approach body temperature during the period of usage. It is manifestly apparent that the cool sensation effected by head 7 be retained through the period of testing which, as suggested, necessitates repeated application. If the mass were relatively small the said rivet would quickly approach body temperature by such repeated application and thus lose its effectiveness. In such an eventuality, the test could not be completed without periods of interruption within which the rivet 6 could be restored to its testing condition. 14 grams has been discovered as a desired weight, but actually experience has taught that a metallic member weighing more than 10 grams has proved adequate for complete testing without interruptions requisite to permit the rivet to return to room temperature.

Accordingly, in view of the foregoing it will be seen that diagnostic instrument A is of marked simplicity of construction, consisting of but two easily produced and interfitted components. However, the metallic element must possess certain critical dimensional and weight properties for efficient and efficaciously effected testing. Furthermore, instrument A is of such limited size as to be transported in a facile manner and thus be usable at any given site, whether within the patient's home, at the scene of an accident, etc., as distinguished from the more complex and bulky devices which have been used heretofore to test cutaneous sensory reaction, all of which require presentation of the patient at the prescribed location of the equipment.

As indicated above, the end of body 1 remote from head 7 is rounded and with like curvature as said head 7. Although such end curvature of body 1 does not bear upon the functionality of the same, such is desirable in order to prevent a patient from differentiating between head 7 and end a by a sensory detection in any geometrical differences. Thus, for instance, with head 7 being rounded and the opposite end of body 1 being of other configuration, such as flat, slightly concave, or even of different convexity, a patient could provide the "correct" answers regardless of the thermal reaction to the instruction ends and thereby frustrate the entire examination.

Having described my invention, what I claim and desire to obtain by Letters Patent is:

1. A diagnostic device for determining the cutaneous sensory reception of a patient by alternatingly applying to a patient's skin, surfaces of the device of materials having different rates of heat transferability comprising an elongated manually manipulate, non-metallic solid body having a bore proceeding from one end and closingly terminating substantially intermediate the length of said body and hence spacedly from the opposite end of said body, a metallic component having a stem portion non-adjustably, fittedly received within said bore and having an integral head of relatively greater cross-section than said stem projecting outwardly of said body one end, said head having an inner surface directed coveringly toward the adjacent end surface of said non-metallic body surrounding the adjacent end of said bore, said head further having a continuous unbroken outer surface defining a first skin applicable surface, said body opposite, integral end being of substantially like area as said metallic component head and having its outer surface defining a second skin applicable surface, the metallic component having a relatively high heat transferability with respect to said non-metallic body.

2. A diagnostic device as defined in claim 1 and further characterized by said metallic component having a mass of 10 or more grams.

3. A diagnostic device as defined in claim 1 and further characterized by the outwardly projecting head of said metallic component having a surface area of approximately 1 cm$^2$ or greater.

4. A diagnostic device as defined in claim 1 and further characterized by the end of said metallic component and the end of said non-metallic body remote from siad component having like configurations.

5. A diagnostic instrument as defined in claim 4 and further characterized by said configuration being convex.

6. A diagnostic device as defined in claim 4 and further characterized by each of said ends being outwardly rounded and formed upon substantially the same radius.

7. A diagnostic device as defined in claim 1 and further characterized by said metallic component head having sufficient mass to prevent relatively rapid approach to body temperature of the patient during application upon the patient's skin.

8. A diagnostic device as defined in claim 1 and further characterized by said elongated non-metallic body being constructed of wood.

9. A diagnostic device as defined in claim 1 and further characterized by said elongated non-metallic body being constructed of plastic.

10. A diagnostic device as defined in claim 1 and further characterized by said elongated non-metallic body being constructed of natural rubber.

11. A diagnostic device as defined in claim 1 and further characterized by said elongated non-metallic body being constructed of synthetic rubber.

* * * * *